US008559696B2

(12) United States Patent
Yamanaka et al.

(10) Patent No.: US 8,559,696 B2
(45) Date of Patent: Oct. 15, 2013

(54) IMAGING METHOD OF STRUCTURE DEFECT, IMAGING DEVICE OF STRUCTURE DEFECT, IMAGING METHOD OF BUBBLE OR LESION AND IMAGING DEVICE OF BUBBLE OR LESION

(75) Inventors: Kazushi Yamanaka, Sendai (JP); Yoshikazu Ohara, Sendai (JP); Yohei Shintaku, Sendai (JP)

(73) Assignee: Tohoku University, Sendai-Shi (JP)

( * ) Notice: Subject to any disclaimer, the term of this patent is extended or adjusted under 35 U.S.C. 154(b) by 414 days.

(21) Appl. No.: 13/054,317

(22) PCT Filed: May 19, 2009

(86) PCT No.: PCT/JP2009/059212
§ 371 (c)(1),
(2), (4) Date: Feb. 4, 2011

(87) PCT Pub. No.: WO2010/007830
PCT Pub. Date: Jan. 21, 2010

(65) Prior Publication Data
US 2011/0123119 A1 May 26, 2011

(30) Foreign Application Priority Data
Jul. 18, 2008 (JP) .................................. 2008-187578

(51) Int. Cl.
*G06K 9/00* (2006.01)
*G01N 29/04* (2006.01)
(52) U.S. Cl.
USPC ............................... 382/141; 73/598; 73/600
(58) Field of Classification Search
USPC ............. 382/141–152; 73/577–583, 597–600
See application file for complete search history.

(56) References Cited

U.S. PATENT DOCUMENTS

| 6,584,847 B1 * | 7/2003 | Hirose ............................. 73/579 |
| 6,672,162 B2 * | 1/2004 | Hirose ............................. 73/579 |
| 2003/0183011 A1 * | 10/2003 | Hirose ............................. 73/597 |

FOREIGN PATENT DOCUMENTS

JP    A-2005-315636    11/2005

OTHER PUBLICATIONS

International Search Report issued in corresponding International Patent Application No. PCT/JP2009/059212 dated Jun. 16, 2009.
Szabo et al., "Diagnostic Ultrasound Imaging; Inside Out," *Academic Pr*, 2004, pp. 171-212 (Chapter 7, 'Array Beamforming').
Ohara et al., "Ultrasonic Evaluation of Closed Cracks Using Subharmonic Phased Array," *Japanese Journal of Applied Physics*, 2008, pp. 3908-3915, vol. 47, No. 5, Japan.
Ohara et al. "Mienai kiretsu o choonpa de sokutei," *Inspection Engineering*, 2008, pp. 8-14, vol. 13, No. 5, Japan (with English-language abstract).
Yamanaka et al., "Tojita kiretsu mo mieru choonpa eizo sochi 'SPACE' no kaihatsu," *Genshiryoku eye*, 2007, pp. 38-41, vol. 53, No. 11, Japan (with English-language abstract).
International Preliminary Report on Patentability issued in corresponding International Application No. PCT/JP2009/059212 dated Mar. 17, 2011.

* cited by examiner

*Primary Examiner* — Brian Le
(74) *Attorney, Agent, or Firm* — Oliff & Berridge, PLC

(57) ABSTRACT

Scattered waves from the defect of burst ultrasonic waves radiated from an ultrasonic transmitter to a structure in two different arrangements of the ultrasonic transmitter and an array receiver are received by the array receiver so as to obtain a reception signal. The reception signal is subjected to a band-pass filter that passes a specific frequency component, shifted by different time according to the position of each reception sensor element of the array receiver and then, added so as to obtain a processing signal. On the basis of the processing signal, an image of the defect is obtained, respectively. A common portion of the obtained two images is extracted.

19 Claims, 11 Drawing Sheets

IMAGING METHOD OF STRUCTURE DEFECT, IMAGING DEVICE OF STRUCTURE DEFECT, IMAGING METHOD OF BUBBLE OR LESION AND IMAGING DEVICE OF BUBBLE OR LESION

TECHNICAL FIELD

The present invention relates to an imaging method of a structure defect that detects a defect such as a crack contained in the structure and an imaging device of a structure defect as well as an imaging method of a bubble or a lesion that detects an bubble or a lesion contained in a tissue and an imaging device of an bubble or a lesion.

BACKGROUND ART

In order to ensure safety of important equipment such as nuclear reactors, aircrafts, railways and the like and to ensure soundness of manufactured materials and joined materials, safety control is executed in which a crack and an incomplete joined surface which cause destruction are detected by reflection or scattering of ultrasonic waves, the size thereof is accurately evaluated and the equipment is replaced if danger is present. However, in a fatigue crack having large crack closure stress that closes a crack surface due to various causes or a closed crack in which an oxidized film is formed on the crack surface caused by stress corrosion crack, reflection/scattering of ultrasonic waves is small, and a measurement error of a length and a depth of a crack is large, which is a problem.

A process of obtaining an image of a crack by adding a signal obtained by giving a different delay according to a position of an element to scattered waves obtained by the reception array element is called a phased-array method, which is known in the field of non-destruction inspection (See Non-Patent Document 1, for example). However, even with an image by the phased-array method, accurate measurement of a closed crack has been difficult.

Under the above circumstances, a quantitative evaluation method of a closed crack using subharmonic waves generated in a closed crack by radiating ultrasonic waves with a large amplitude and a quantitative evaluating device of a closed crack are proposed (See Patent Document 1, for example). With this evaluation method and evaluating device, by applying the phased array method to the subharmonic waves, a closed crack can be imaged. This method is named SPACE (Subharmonic Phased Array for Crack Evaluation) (See Non-Patent Document 2, for example).

FIG. 14 is a principle diagram of the SPACE. In the SPACE, a transmission-side probe (transmitter) using a $LiNbO_3$ single crystal oscillator with excellent pressure resistance that can generate ultrasonic waves with a large amplitude, an array receiver for imaging, and a frequency pass filter (digital filter) are used as an element technology. By radiating large-amplitude ultrasonic waves (frequency f) from the transmission-side probe, in addition to linear scattering of fundamental waves (frequency f) at an open crack, subharmonic waves (frequency f/2) are generated since the closed crack surface is opened by tensile stress of the large-amplitude ultrasonic waves at the closed crack and opened/closed oscillated. The waves are received by the array receiver, and components are separated by the digital filter so that a fundamental wave image and a subharmonic wave image can be observed. If a crack distal end is closed, a crack depth might be underestimated with the fundamental wave image, but it can be accurately measured with the subharmonic wave image.

CITATION LIST

Patent Literature

[Patent Document 1] Japanese Patent Laid-Open No. 2005-315636

Non-Patent Literature

[Non-Patent Document 1] "Diagnostic Ultrasound Imaging; Inside Out" by T. L. Szabo, Academic Pr, Sep. 7, 2004, p. 171

[Non-Patent Document 2] "Ultrasonic Evaluation of Closed Cracks Using Subharmonic Phased Array" by Yoshikazu Ohara, Setsu Yamamoto, Tsuyoshi Mihara, and Kazushi Yamanaka, Japanese Journal of Applied Physics, 2008, 47, p. 3908-3915

SUMMARY OF INVENTION

Technical Problem

In the SPACE shown in FIG. 14, if high spatial resolution is required, burst waves having the cycle number 3 or less are used as incident waves. At this time, since frequency resolution is lowered, if a non-linear scattering source (closed crack) and a linear scattering source (bottom surface/open crack) are close to each other or a response from the linear scattering source is stronger than the non-linear scattering source, not only the open crack but also a fundamental wave component that could not be fully removed by the filter appear in the subharmonic image. As a result, it becomes difficult to discriminate a closed crack from an open crack, and discrimination is deteriorated, which is a problem. The burst waves are waves composed of sine waves having a plurality of cycle numbers. Waves composed of the sine waves having one cycle number are pulse waves.

The present invention has an object to provide an imaging method of a structure defect and an imaging device of a structure defect that have high frequency resolution and spatial resolution and can improve discrimination between a closed crack and an open crack. Also, another object of the present invention is, on the basis of the same principle, to provide an imaging method of a bubble or a lesion and an imaging device of a bubble or a lesion that have high frequency resolution and spatial resolution and can improve discrimination between tissues and a bubble as well as a lesion.

Solution to Problem

In order to achieve the above objects, the imaging method of a structure defect according to the present invention is an imaging method of a structure defect that detects a defect such as a crack contained in a structure, having an ultrasonic transmitter that radiates burst ultrasonic waves composed of sine waves of a predetermined cycle number and an array receiver having a plurality of reception sensor elements, composed of, in first arrangement in which the ultrasonic transmitter and the array receiver are arranged at predetermined positions with respect to the defect, a first reception process of receiving scattered waves from the defect of the burst ultrasonic waves radiated from the ultrasonic transmitter to the structure by the array receiver so as to obtain a first reception signal, a first imaging process in which the first reception signal is subjected to a band-pass filter that passes a specific frequency component and is shifted by different time according to the position of each of the reception sensor elements of the array receiver and then, added so as to obtain a first processing signal, and a first image of the defect is obtained on the basis of the obtained first processing signal, in second arrangement in which at least one of the positions of the ultrasonic transmitter and the array receiver with respect to the defect is different, a second reception process of receiving the scattered waves from the defect of the burst ultrasonic waves radiated from the ultrasonic transmitter to the structure by the array receiver so as to obtain a second reception signal, a second imaging process in which the second reception signal is subjected to the band-pass filter and is shifted by different time according to the position of each of the reception sensor elements of the array receiver and then, added so as to obtain a second processing signal, and a second image of the defect is obtained on the basis of the obtained second processing signal, and an extraction process of extracting a common portion of the first image and the second image.

The principle of the imaging method of a structure defect according to the present invention will be described referring to FIG. 1.

FIG. 1A is an image on the basis of subharmonic waves separated from scattered waves obtained when short burst ultrasonic waves with high temporal resolution (burst ultrasonic waves with smaller cycle number) are made to enter a closed part and an open part of a crack from the ultrasonic transmitter on the left side are detected using the array receiver on the right side in the two array receivers and corresponds to the SPACE shown in FIG. 14. The detected scattered waves are subjected to the band-pass filter so as to separate the subharmonic waves, and an image of the crack is obtained further using the phased array method. If the closed part and the open part of the crack are away from each other or if signal intensity of the open part is small, as shown by a solid line in FIG. 1A, the open part is not visible, and only the closed part is selectively imaged. However, if the closed part and the open part of the crack are close to each other or the signal intensity of the open part is large, as shown by a broken line in FIG. 1A, not only the closed part but the open part are also visible in some cases. This is due to low frequency resolution and more specifically, as shown in FIG. 1E, a signal of the fundamental waves with the center frequency f generated from the open part has a wide-band spectrum and leaks to the frequency f/2 of the subharmonic waves. The open part seen in the image of the subharmonic waves showing only the closed crack is originally a kind of a ghost, which results in deterioration in selectivity of the closed crack and the open crack.

On the other hand, FIGS. 1B to 1D show the imaging method of a structure defect according to the present invention. FIGS. 1B and 1C are images on the basis of the subharmonic waves separated from the scattered waves when the scattered waves obtained when long burst ultrasonic waves (burst ultrasonic waves with large cycle number) are made to enter the closed part and the open part of the crack from the ultrasonic transmitter are detected using the array receivers on the right side and the left side, respectively. In this case, too, the detected scattered waves are subjected to the band-pass filter so as to separate the subharmonic waves, and an image of the crack is obtained further using the phased array method. As shown in FIGS. 1B and 1C, even if the closed part and the open part of the crack are close to each other or if the signal intensity of the open part is large, only the closed part is visible, while the open part is not visible, and selectivity is improved. This is because frequency resolution is high and more specifically, as shown in FIG. 1F, the signal of the fundamental waves with the central frequency f generated from the open part has a narrow-band spectrum and does not leak to the frequency f/2 of the subharmonic waves.

However, as shown in FIGS. 1B and 1C, the image of the crack extends in a direction connecting the crack and the center of the array receiver. The phenomenon that the image extends in one direction as above is found out by the inventors, and that deteriorates the spatial resolution. Thus, as shown in FIG. 1D, by extracting a common portion of a first image shown in FIG. 13 and a second image shown in FIG. 1C, an image of a true closed part with improved spatial resolution can be obtained. Also, the open part as a ghost seen in FIG. 1A is not visible, and selectivity is improved.

As described above, the imaging method of a structure defect according to the present invention has high frequency resolution and spatial resolution and can improve discrimination between a closed crack and an open crack. Also, a defect such as a closed crack can be detected with high accuracy. In the imaging method of a structure defect according to the present invention, the first arrangement and the second arrangement may be different only by the position of the ultrasonic transmitter, only by the position of the array receiver or by the positions of both the ultrasonic transmitter and the array receiver. In any case, since the direction in which the image of the defect obtained by the first arrangement extends is different from the direction in which the image of the defect obtained by the second arrangement extends, by extracting the common portion of the two images, an image of the defect such as a closed crack with improved spatial resolution can be obtained.

The imaging device of a structure defect according to the present invention is an imaging device of a structure defect that detects a defect such as a crack contained in a structure, composed of an ultrasonic transmitter that radiates burst ultrasonic waves composed of sine waves with an arbitrary cycle number, an array receiver having a plurality of reception sensor elements disposed capable of receiving scattered waves from the defect of the burst ultrasonic waves radiated from the ultrasonic transmitter to the structure, imaging means in which a reception signal received by each of the reception sensor elements of the array receiver is subjected to a band-pass filter that passes a specific frequency component and shifted by different time according to the position of each of the reception sensor elements of the array receiver and then, added so as to obtain a processing signal and on the basis of the obtained processing signal, an image of the defect is obtained, and extracting means that extracts a common portion of two images different from each other obtained by the imaging means.

The imaging device of a structure defect according to the present invention can easily perform the imaging method of a structure defect according to the present invention. Thus, the imaging device of a structure defect according to the present invention has high frequency resolution and spatial resolution and can improve discrimination between a closed crack and an open crack. Also, a defect such as a closed crack can be detected with high accuracy.

The imaging method of a structure defect according to the present invention preferably has sine waves with four or more cycle number contained in the burst ultrasonic waves. Also, in the imaging device of a structure defect according to the present invention, the ultrasonic transmitter is preferably constituted so as to radiate the burst ultrasonic waves with four or more cycle number of sine waves, and the imaging means is preferably constituted so that two images different from each other are obtained for two cases in which the position of at least one of the ultrasonic transmitter and the array receiver is different with respect to the defect. In this case, particularly frequency resolution can be improved, and discrimination between the closed crack and the open crack is excellent. Also, a defect such as a closed crack can be detected with particularly high accuracy.

The imaging method of a structure defect according to the present invention may constitute the first arrangement and the second arrangement by switching the reception sensor elements used in the array receiver. Also, in the imaging device of a structure defect according to the present invention, the array receiver may be capable of switching the reception sensor element to be used. In this case, two different images can be obtained without moving neither the ultrasonic transmitter nor the array receiver, and an image of a defect such as a closed crack can be easily obtained with improved spatial resolution.

The imaging method of a structure defect according to the present invention is an imaging method of a structure defect that detects a defect such as a crack contained in a structure, having an ultrasonic transmitter that radiates burst ultrasonic waves composed of sine waves with an arbitrary cycle number and an array receiver having a plurality of reception sensor elements, may have a first reception process in which first burst ultrasonic waves composed of sine waves with a predetermined cycle number are radiated from the ultrasonic transmitter to the structure, and the scattered waves from the defect of the first burst ultrasonic waves are received by the array receiver so as to obtain a first reception signal, a first imaging process in which the first reception signal is subjected to a band-pass filter that passes a center frequency component of the sine waves, a frequency component of the integral multiple thereof or a frequency component of an integral fraction thereof and shifted by different time according to the position of each of the reception sensor elements of the array receiver and then, added so as to obtain a first processing signal and on the basis of the obtained first processing signal, a first image of the defect is obtained, a second reception process in which second burst ultrasonic waves composed of sine waves of a cycle number different from the predetermined cycle number are radiated from the ultrasonic transmitter to the structure, and the scattered waves from the defect of the second burst ultrasonic waves are received by the array receiver so as to obtain a second reception signal, a second imaging process in which the second reception signal is subjected to the band-pass filter and shifted by different time according to the position of each of the reception sensor elements of the array receiver and then, added so as to obtain a second processing signal, and on the basis of the obtained second processing signal, a second image of the defect is obtained, and an extraction process of extracting a common portion of the first image and the second image.

The principle of the imaging method of a structure defect according to the present invention if two burst ultrasonic waves of the sine waves with different cycle numbers will be described referring to FIG. 2.

FIG. 2A shows an image on the basis of subharmonic waves separated from the scatted waves if scattered waves obtained when short burst ultrasonic waves with high temporal resolution (burst ultrasonic waves with smaller cycle number) are made to enter a closed part and an open part of a crack from the ultrasonic transmitter are detected using the array receiver. The detected scattered waves are subjected to the band-pass filter so as to separate the subharmonic waves, and an image of the crack is obtained further using the phased array method. In the image in FIG. 2A, not only the closed part but also the open part is visible. FIG. 2B is an image on the basis of the subharmonic waves by the long burst ultrasonic waves (burst ultrasonic waves with large cycle number), and only the closed part is visible, but the open part is not visible. However, the image extends to the direction of the center of the array receiver. FIG. 2C is an image obtained by extracting the common portion of a first image shown in FIG. 2A and a second image shown in FIG. 2B and illustrates that the open part is erased and an image of a true closed part with improved spatial resolution can be obtained.

As described above, the imaging method of a structure defect according to the present invention of the case in which the two burst ultrasonic waves of the sine waves with different cycle numbers are radiated has high frequency resolution and spatial resolution and can improve discrimination between a closed crack and an open crack. Also the defect such as a closed crack can be detected with high accuracy. The imaging method of a structure defect according to the present invention can be easily performed by the imaging device of a structure defect according to the present invention. With the method shown in FIG. 2, since a common portion of two images extending in the same direction though the lengths are different is extracted, an image becomes larger than the method in FIG. 1 in which a common portion of the images extending in different directions is extracted, and spatial resolution might be lower.

The imaging method of a structure defect according to the present invention of the case in which the two burst ultrasonic waves of sine waves with different cycle numbers are radiated preferably has four or more cycle numbers of the sine waves contained in the first burst ultrasonic waves and three or less cycle numbers of the sine waves contained in the second burst ultrasonic waves. Also, in the imaging device of a structure defect according to the present invention, in the cases in which the cycle numbers of the sine waves contained in the burst ultrasonic waves radiated by the ultrasonic transmitter are four or more and three or less, the imaging means is preferably constituted so that two images different from each other can be obtained. In this case, particularly the frequency resolution and spatial resolution can be improved at the same time, and discrimination between the closed crack and the open crack is excellent. Also, the defect such as a closed crack can be detected with particularly high accuracy.

In the imaging method of a structure defect according to the present invention, a band width of the band-pass filter may be set in inverse proportion to the cycle number of sine waves contained in the burst ultrasonic waves corresponding to the first reception signal or the second reception signal subjected to the filter. Also, in the imaging device of a structure defect according to the present invention, the imaging means may have a band width of the band-pass filter in inverse proportion to the cycle number of sine waves contained in the burst ultrasonic waves corresponding to the reception signal subjected to the filter. In this case, particularly the frequency resolution can be improved, and discrimination between the closed crack and the open crack is excellent. Also, the defect such as a closed crack can be detected with particularly high accuracy.

In the imaging method of a structure defect according to the present invention, the number of the reception sensor elements of the array receiver may be determined so that the first image and the second image are in the shape extending depending on the cycle number of the sine waves contained in the burst ultrasonic waves corresponding to each image in the direction connecting the center of the array receiver and the defect. Also, in the imaging device of a structure defect according to the present invention, the number of the reception sensor elements in the array receiver may be determined so that the two images are in the shape extending depending on the cycle number of the sine waves contained in the burst ultrasonic waves corresponding to each image in the direction connecting the center of the array receiver and the defect. In this case, the spatial resolution can be particularly improved. Also, the defect such as a closed crack can be detected with particularly high accuracy.

In the imaging method of a structure defect according to the present invention, the band-pass filter may pass only a frequency component of harmonic waves having a frequency of integral multiple of the frequency of the sine waves contained in the burst ultrasonic waves corresponding to the first reception signal or the second reception signal subjected to the filter or of subharmonic waves having an integral fraction of the frequency of the sine waves contained in the burst ultrasonic waves corresponding to the first reception signal or the second reception signal subjected to the filter. Also, in the imaging device of a structure defect according to the present invention, the band-pass filter may be constituted such that only a frequency component of harmonic waves having a frequency of integral multiple of the frequency of the sine waves contained in the burst ultrasonic waves corresponding to the reception signal subjected to the filter or subharmonic waves having a frequency of an integral fraction of the frequency of the sine waves contained in the burst ultrasonic waves corresponding to the reception signal subjected to the filter. In this case, the frequency resolution can be particularly improved. Also, the defect such as a closed crack can be detected with particularly high accuracy using only the harmonic waves or subharmonic waves.

In the imaging method of a structure defect according to the present invention, the extraction process may be constituted such that by calculating the product of the digitized first image and the second image or by calculating a square root of the product, or by giving intensity of the original first image or second image only to a common part of a portion to become one of the binarized first image or second image, the common portion of the first image and the second image is extracted. Also, in the imaging device of a structure defect according to the present invention, the extracting means may be constituted such that by calculating the product of the digitized two images or by calculating a square root of the product, or by giving intensity of the original image only to a common part of a portion to become one of the binarized two images, a common portion of each image is extracted. In these cases, a common portion of each image can be easily extracted using a computer, and a defect such as a closed crack can be detected with high accuracy.

According to the imaging method of a structure defect and the imaging device of a structure defect according to the present invention, in a site of nondestructive evaluation such as nuclear reactors, aircrafts, railways, a manufacturing process of a material, a joining process and the like, a closed crack can be imaged. Also, as a result, necessity of repair/replacement can be shown quantitatively, and contribution can be made to establishment of safety and security of the equipment and structures. The imaging method of a structure defect and the imaging device of a structure defect according to the present invention can also detect an open crack with high accuracy by using short burst ultrasonic waves (burst ultrasonic waves with smaller cycle number) with high temporal resolution.

An imaging method of a bubble or a lesion according to the present invention is an imaging method of a bubble or a lesion that detects a bubble or a lesion contained in a tissue, having an ultrasonic transmitter that radiates burst ultrasonic waves composed of sine waves with an arbitrary cycle number and an array receiver having a plurality of reception sensor elements, composed of a first reception process in which first burst ultrasonic waves composed of sine waves with a predetermined cycle number are radiated from the ultrasonic transmitter to the tissue and scattered waves from the bubble or lesions of the first burst ultrasonic waves are received by the array receiver so as to obtain a first reception signal, a first imaging process in which the first reception signal is subjected to a band-pass filter that passes a center frequency component of the sine waves, a frequency component of the integral multiple thereof or a frequency component of an integral fraction thereof and shifted by different time according to the position of each of the reception sensor elements of the array receiver and then, added so as to obtain a first processing signal and on the basis of the obtained first processing signal, a first image of the bubble or lesion is obtained, a second reception process in which second burst ultrasonic waves composed of sine waves of a cycle number different from the predetermined cycle number are radiated from the ultrasonic transmitter to the tissue, and the scattered waves from the bubble or lesion of the second burst ultrasonic waves are received by the array receiver so as to obtain a second reception signal, a second imaging process in which the second reception signal is subjected to the band-pass filter and shifted by different time according to the position of each of the reception sensor elements of the array receiver and then, added so as to obtain a second processing signal, and on the basis of the obtained second processing signal, a second image of the air bubble or lesion is obtained, and an extraction process of extracting a common portion of the first image and the second image.

The imaging device of a bubble or a lesion according to the present invention is an imaging device of a bubble or a lesion that detects a bubble or a lesion contained in a tissue, having an ultrasonic transmitter that radiates burst ultrasonic waves composed of sine waves with an arbitrary cycle number, an array receiver having a plurality of reception sensor elements disposed capable of receiving scattered waves from the bubble or lesion of the burst ultrasonic waves radiated from the ultrasonic transmitter to the tissue, imaging means in which a reception signal received by each of the reception sensor elements of the array receiver is subjected to a band-pass filter that passes a specific frequency component and shifted by different time according to the position of each of the reception sensor elements of the array receiver and then, added so as to obtain a processing signal and on the basis of the obtained processing signal, an image of the bubble or lesion is obtained, and extracting means that extracts a common portion of two images different from each other obtained by the imaging means.

It is obvious that the imaging method of a bubble or a lesion and the imaging device of a bubble or a lesion according to the present invention can be similarly applied to improvement of selectivity of an imaging agent a bubble or a lesion of a living tissue using harmonic/subharmonic waves, not only to a structure defect, by reading the "structure" as "tissue" and the "defect" as "a bubble or a lesion" in the description of the imaging method of a structure defect and the imaging device of a structure defect according to the present invention. Thus, the imaging method of a bubble or a lesion and the imaging device of a bubble or a lesion according to the present invention have high frequency resolution and spatial resolution and can improve discrimination between the tissue and the bubble as well as lesion.

Advantageous Effects of Invention

According to the present invention, the imaging method of a structure defect and the imaging device of a structure defect that have high frequency resolution and spatial resolution and can improve discrimination between a closed crack and an open crack can be provided. Also, on the basis of the same principle, the imaging method of a bubble or a lesion and the imaging device of a bubble or a lesion that have high frequency resolution and spatial resolution and can improve discrimination between the tissue and the bubble as well as the lesion can be provided.

DESCRIPTION OF EMBODIMENTS

An embodiment of the present invention will be described below referring to the attached drawings.

FIGS. 3 to 13 illustrate the imaging method of a structure defect and the imaging device of a structure defect of the embodiment of the present invention.

Figure 1:
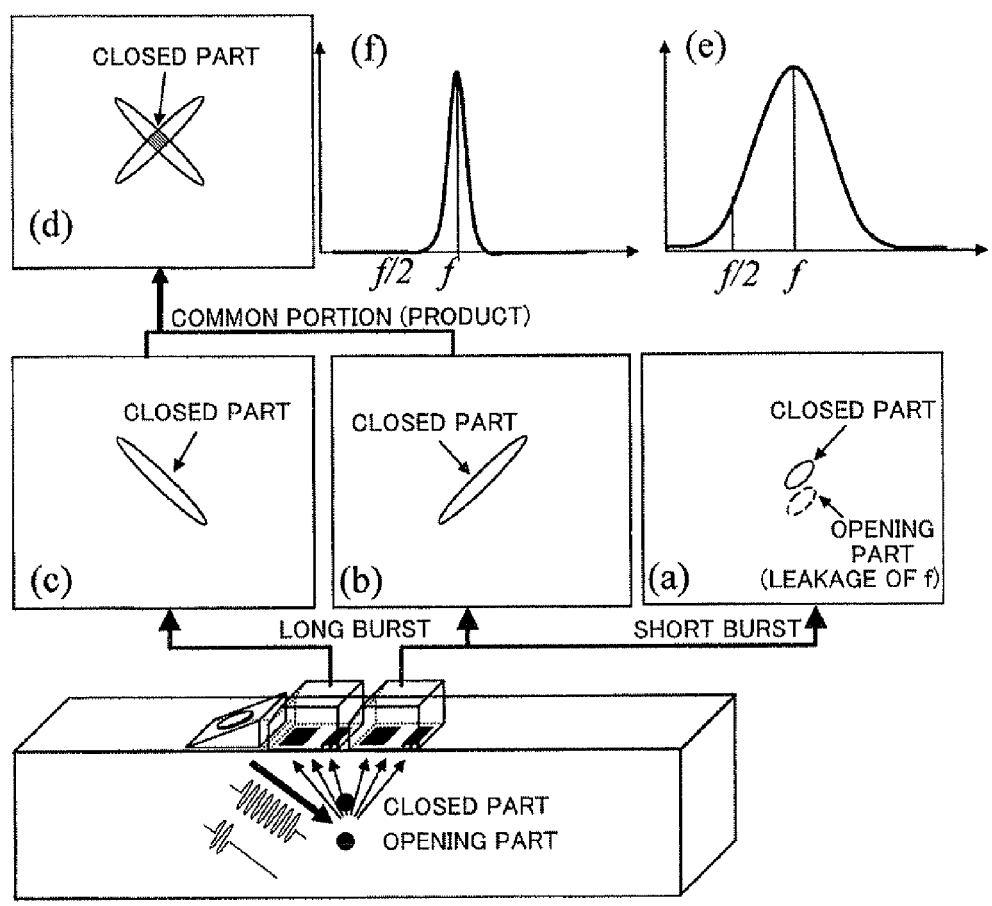
FIG. 1 is a principle diagram illustrating an imaging method of a structure defect according to claim 1 of the present invention.
Figure 2:
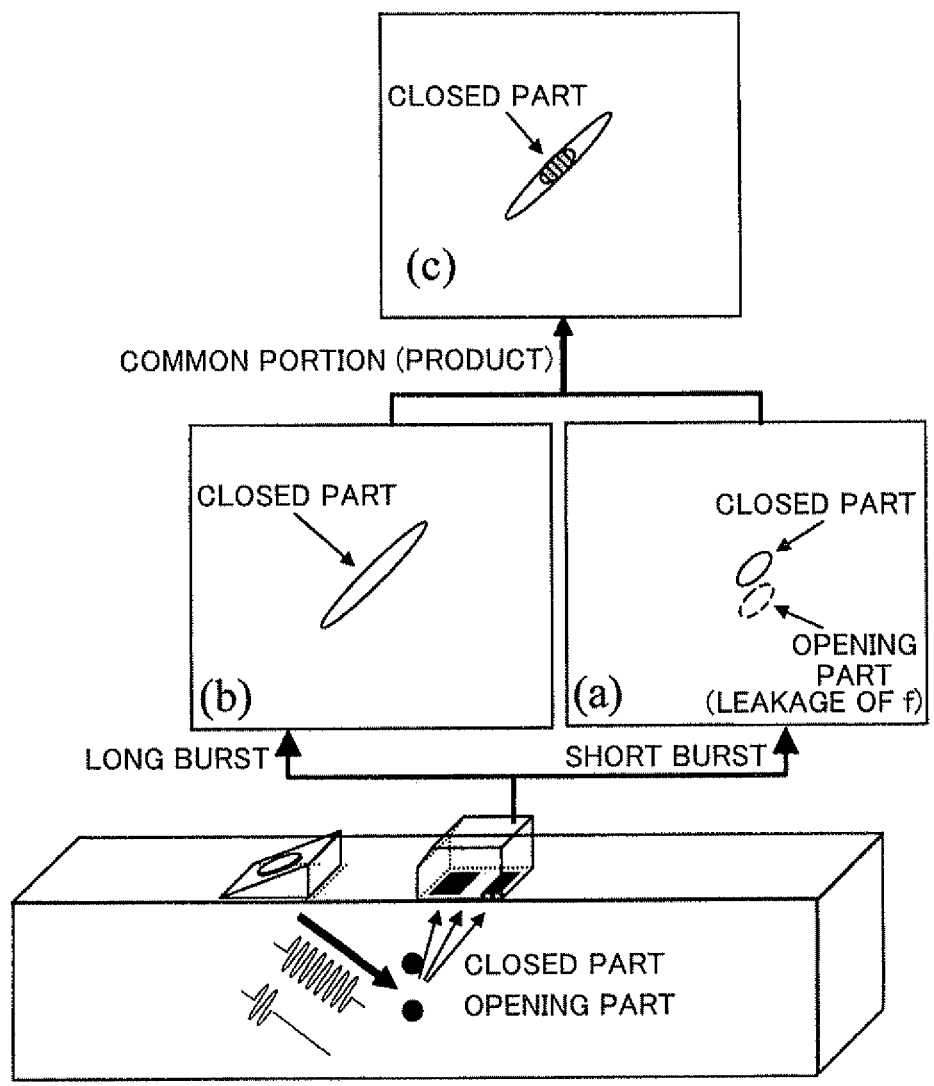
FIG. 2 is a principle diagram illustrating an imaging method of a structure defect according to claim 2 of the present invention.
Figure 3:
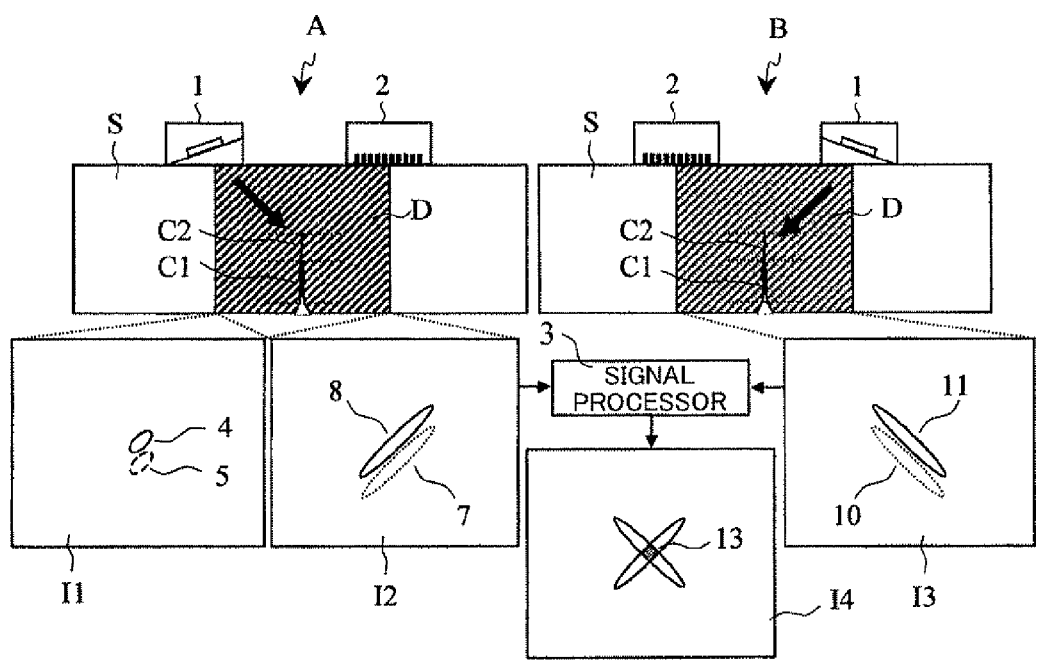
FIG. 3 is a longitudinal sectional view illustrating the imaging method of a structure defect and an imaging device of a structure defect of an embodiment of the present invention and obtained images.

As shown in FIG. 3, the imaging device of a structure defect has an ultrasonic transmitter 1, an array receiver 2, and a signal processor 3.

The ultrasonic transmitter 1 is configured to be able to radiate burst ultrasonic waves composed of sine waves with an arbitrary cycle number. The ultrasonic transmitter 1 is arranged to radiate the burst waves with an arbitrary cycle number to a crack continuously including an open crack C1 and a closed crack C2 in a sample S of a structure.

The array receiver 2 has a plurality of reception sensor elements. The array receiver 2 is disposed to be able to receive scattered waves from the crack of the burst ultrasonic waves radiated from the ultrasonic transmitter 1 to the sample S in the structure, that is, linear scattered waves generated at a distal end portion of the open crack C1 and subharmonic waves generated in the closed crack C2.

The signal processor 3 is composed of a computer connected to the array receiver 2 and has imaging means (not shown) and extracting means (not shown). The imaging means subjects the reception signal received by each reception sensor element of the array receiver 2 to a band-pass filter that passes a specific frequency component and obtains an image of the crack using the phased array method for the signal having passed through the band-pass filter. That is, the imaging means shifts the signal having passed through the band-pass filter by different time according to the position of each reception sensor element of the array receiver 2 and then, adds and obtains a processing signal, and on the basis of the obtained processing signal, obtains an image of the crack. The imaging means has the band width of the band-pass filter in inverse proportion to the cycle number of the sine waves contained in the burst ultrasonic waves corresponding to the reception signal to be filtered. Also, the band-pass filter is configured to pass only the frequency component of subharmonic waves having a frequency of an integral fraction of the frequency of the sine waves contained in the burst ultrasonic waves corresponding to the reception signal to be filtered.

The extracting means extracts a common portion of two images different from each other obtained by the imaging means. In an example shown in FIG. 3, a common portion of an image obtained from the imaging device of a structure defect of a first arrangement A and an image obtained from the imaging device of a structure defect of a second arrangement B is extracted.

In the array receiver 2, the number of reception sensor elements is determined so that the obtained two images are in the shape extending depending on the cycle number of the sine waves contained in the burst ultrasonic waves corresponding to each image in the direction connecting the center of the array receiver 2 and the defect.

The imaging device of a structure defect of the embodiment of the present invention can easily perform the imaging method of a structure defect of the embodiment of the present invention.

As shown in FIG. 3, in the imaging device of a structure defect of the first arrangement A in which the ultrasonic transmitter 1 and the array receiver 2 are arranged at predetermined positions with respect to the crack, burst ultrasonic waves with the cycle number 3 or less are radiated from the ultrasonic transmitter 1 to the crack, and a reception signal in which linear scattered waves generated in the distal end portion of the open crack C1 and the subharmonic waves generated in the closed crack C2 are combined is received by the array receiver 2. By performing imaging by the imaging means within a range of shaded part D on the basis of the subharmonic waves extracted by subjecting the reception signal to the band-pass filter, a subharmonic wave image I1 is obtained. In the subharmonic wave image I1, not only a solid line 4 obtained by imaging the closed crack C2 but also a broken line 5 appears as leakage of the linear scattered waves generated in the open crack C1.

Then, in the imaging device of a structure defect of the first arrangement A, the long burst ultrasonic waves with the cycle number 4 or more of the sine waves are radiated by the ultrasonic transmitter 1 to the crack, and a first reception signal in which the linear scattered waves generated in the distal end portion of the open crack C1 and the subharmonic waves generated in the closed crack C2 are combined is received by the array receiver 2. By performing the imaging by the imaging means within the range of the shaded part D on the basis of the subharmonic waves extracted by subjecting the first reception signal to the band-pass filter, a subharmonic wave image I2 is obtained. In the subharmonic wave image I2, due to the use of the long burst ultrasonic waves, leakage of the linear scattered waves generated in the open crack C1 does not appear (dotted line 7) but only a solid line 8 obtained by imaging the closed crack C2 appears.

However, as a side effect, as a solid line 8 of the subharmonic wave image I2, spatial resolution is deteriorated due to extension of the image with increase of the cycle number. When an attention is paid to the fact that the extension is in a direction connecting the center of the array receiver 2 and the scattering source, it is known that an image with a different extending direction can be obtained by performing the imaging in the different arrangement of the array receiver 2.

Then, as an example, as shown in FIG. 3, the imaging device of a structure defect of the second arrangement B in which the arrangement of the ultrasonic transmitter 1 and the array receiver 2 are reversed with respect to the crack is used. In the imaging device of a structure defect of this second arrangement B, the long burst ultrasonic waves with the same cycle number are radiated by the ultrasonic transmitter 1 to the crack, and a second reception signal in which the linear scattered waves generated in the distal end portion of the open crack C1 and the subharmonic waves generated in the closed crack C2 are combined is received by the array receiver 2. By performing the imaging in the range of the shaded part D by the imaging means on the basis of the subharmonic waves extracted by subjecting the second reception signal to the band-pass filter, a subharmonic wave image I3 is obtained. In the subharmonic wave image I3, due to the use of the long burst ultrasonic waves, leakage of the linear scattered waves generated in the open crack C1 does not appear (dotted line 10) but only a solid line 11 obtained by imaging the closed crack C2 appears.

From the subharmonic wave images I2 and I3 obtained from the first arrangement A and the second arrangement B different from each other, an image I4 for which a common portion is extracted by the extracting means of the signal processor 3 is generated. As a result, the common portion I3 is extracted as a closed part of the crack, and an image of only the crack closed part can be obtained. As described above, according to the imaging method of a structure defect and the imaging device of a structure defect of the embodiment of the present invention, an image of a true closed part with improved spatial resolution can be obtained, and a defect such as a closed crack can be detected with high accuracy. Also, high frequency resolution and spatial resolution are provided, and discrimination between a closed crack and an open crack can be improved.

Subsequently, by means of the extracting means, as an example of a method of extracting a common portion, a simulation was performed for a case of producing a product of two images.

Figure 4:
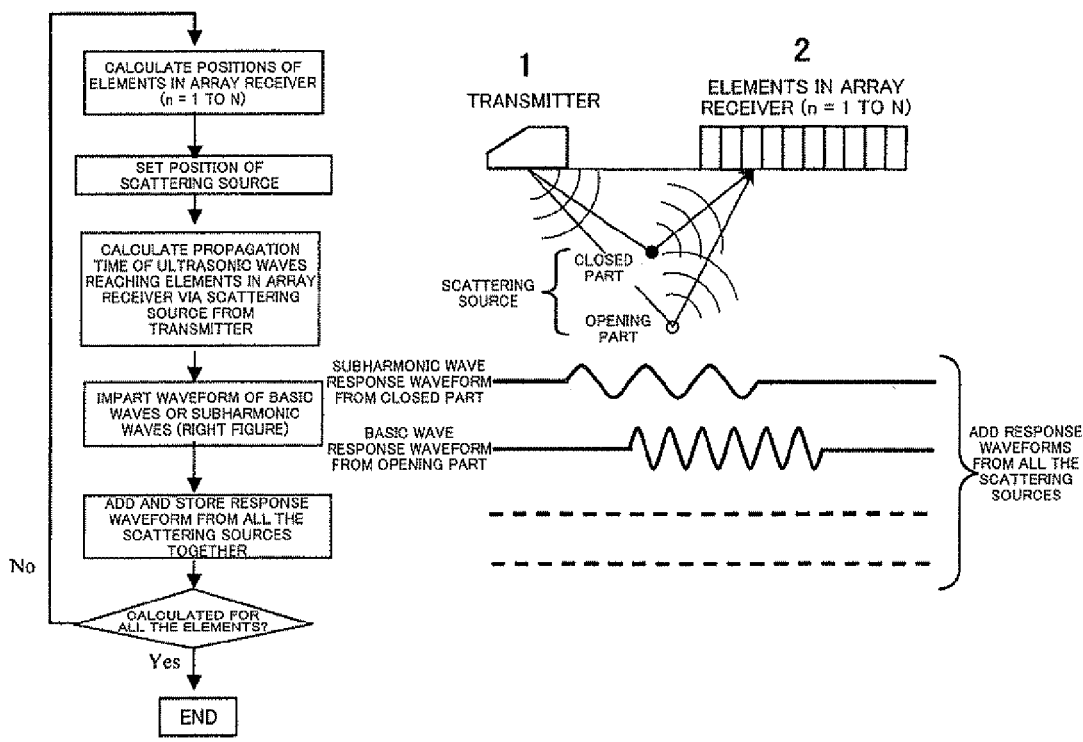
FIG. 4 is a flowchart illustrating a simulation method that creates a reception signal received by an array receiver in the imaging method of a structure defect and the imaging device of a structure defect of the embodiment of the present invention and explanatory diagram.

FIG. 4 illustrates a simulation method of creating a reception signal. First, a position of each reception sensor element (n=1 to N) of the array receiver 2 is calculated. Then, the position of the scattering source is set. Then, on the basis of the positional information, propagation time till when incident waves radiated from the ultrasonic transmitter 1 is scattered by the scattering source and reach the predetermined reception sensor element of the array receiver 2 is calculated, and depending on whether the scattering source is a closed part or an open part, as shown in FIG. 4, a waveform of subharmonic waves or fundamental waves is given. This is repeated for all the scattering sources, the waveform is added/stored and the procedure goes to the subsequent reception sensor element. When the calculation of all the reception sensor elements is finished, these are stored as a reception signal, and the procedure is finished.

Figure 5:
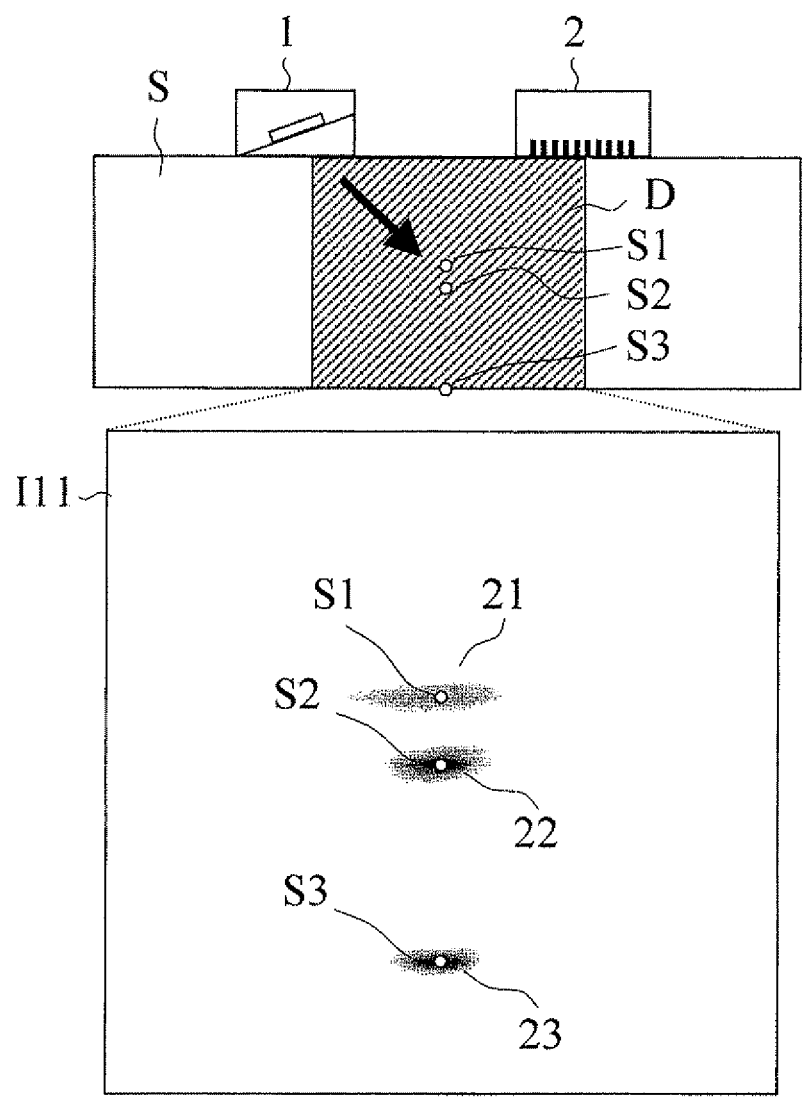
FIG. 5 is a longitudinal sectional view illustrating a configuration of the imaging method of a structure defect and the imaging device of a structure defect simulated in the simulation shown in FIG. 4 and an image obtained by using burst ultrasonic waves with the cycle number 2.

FIG. 5 is a configuration diagram illustrating an example of the imaging device of a structure defect assumed in the simulation and an image obtained by that. As shown in FIG. 5, in the imaging device of a structure defect, the burst ultrasonic waves with the cycle number 2 were radiated by the ultrasonic transmitter 1 to a scattering source S1 that generates subharmonic waves corresponding to a closed crack, a linear scattering source S2 that generates fundamental waves simulating an open crack, and a linear scattering source S3 that generates fundamental waves simulating a bottom surface. However, intensity of S1 is assumed to be ½ of S2 and S3. Subsequently, subharmonic waves generated in the closed crack S1, the linear scattered waves generated in the open crack S2, and the linear scattered waves generated in the bottom surface S3 were received by the array receiver 2.

By performing the imaging by the imaging means on the basis of the reception signal, an image I11 including the subharmonic waves and the linear scattered waves was obtained. However, herein the band-pass filter was set so that both the fundamental waves and the subharmonic waves are transmitted. In the image the closed crack S1 is imaged as 21, the open crack S2 as 22 and the bottom surface S3 as 23.

Figure 6:
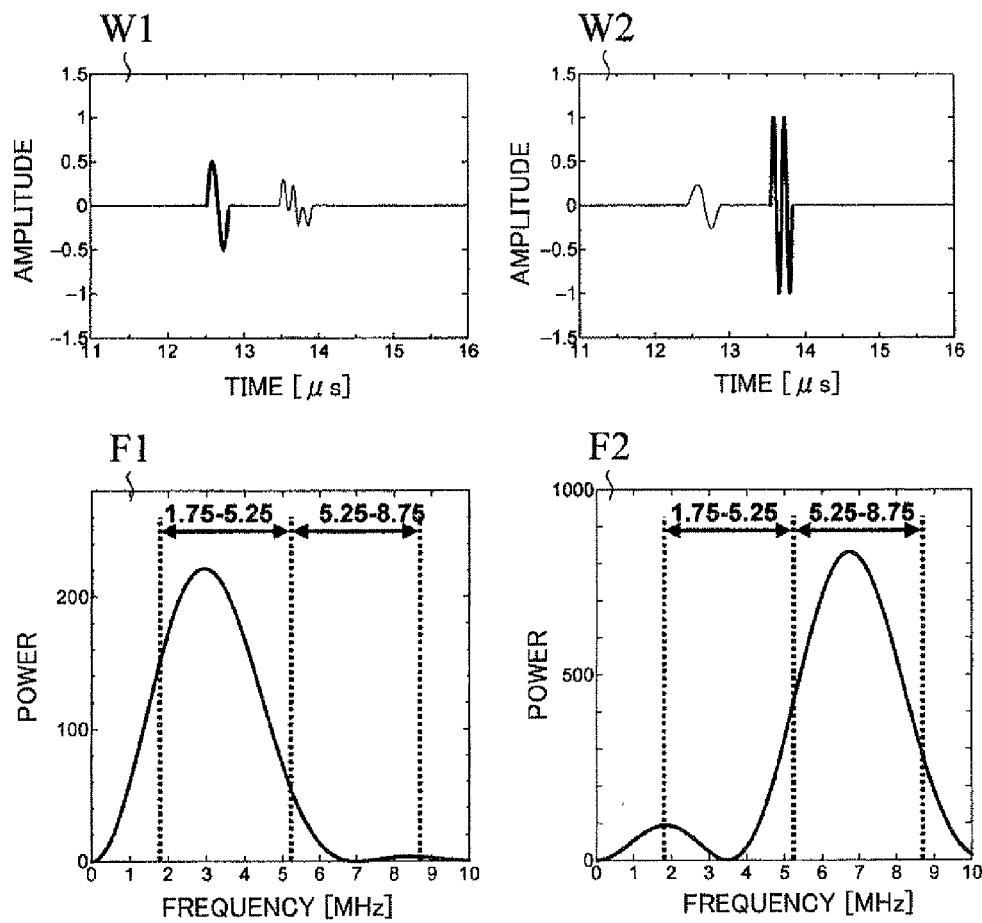
FIG. 6 are a phase-matched waveform W1 (bold line part) corresponding to a closed crack, power spectrum F1 thereof, a phase-matched waveform W2 (bold line part) corresponding to an open crack, and power spectrum F2 thereof if the burst ultrasonic waves with the cycle number 2 are used in the imaging method of a structure defect and the imaging device of a structure defect shown in FIG. 5.

FIG. 6 illustrate a phase matched waveform W1 (bold line part) in 21 imaged from the closed crack S1 and its power spectrum F1 and a phase-matched waveform W2 (bold line part) in 22 imaged from the open crack S2 and its power spectrum F2 in the image I11. As shown by the power spectra F1 and F2 in FIG. 6, since the burst ultrasonic waves with the cycle number 2 with lower frequency resolution, it is known that a frequency characteristic of a wide band is provided.

Figure 7:
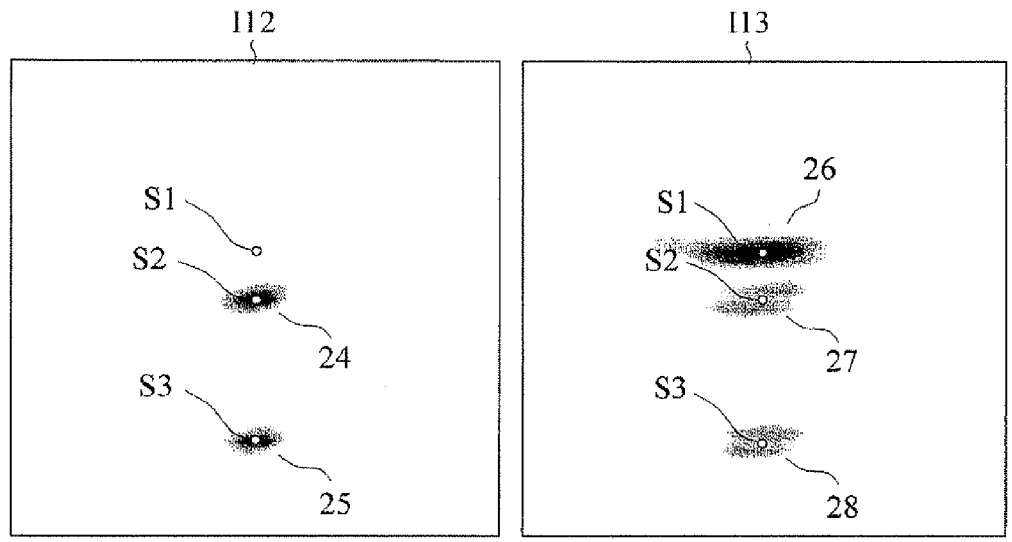
FIG. 7 are a fundamental wave image on the basis of a component of linear scattered waves extracted by a band-pass filter and a subharmonic wave image on the basis of subharmonic waves extracted by the band-pass filter if the burst ultrasonic waves with the cycle number 2 is used in the imaging method of a structure defect and the imaging device of a structure defect shown in FIG. 5.

FIG. 7 illustrates a fundamental wave image I12 on the basis of a component of the linear scattered waves extracted by the band-pass filter and a subharmonic wave image I13 on the basis of the subharmonic waves extracted by the band-pass filter from the signal received by the array receiver 2. As shown in FIG. 7, in the fundamental wave image I12, 24 imaged from the open crack S2 and 25 imaged from the bottom surface S3 appeared. In the subharmonic wave image I13, not only 26 imaged from the closed crack S1 but also 27 and 28 as leakage of the linear scattered waves generated in the open crack S2 and the bottom surface S3 appeared. Under this condition, intensity ratio between S1 and S2 in the subharmonic wave image I13 representing discrimination of the closed crack is 2.4.

Figure 8:
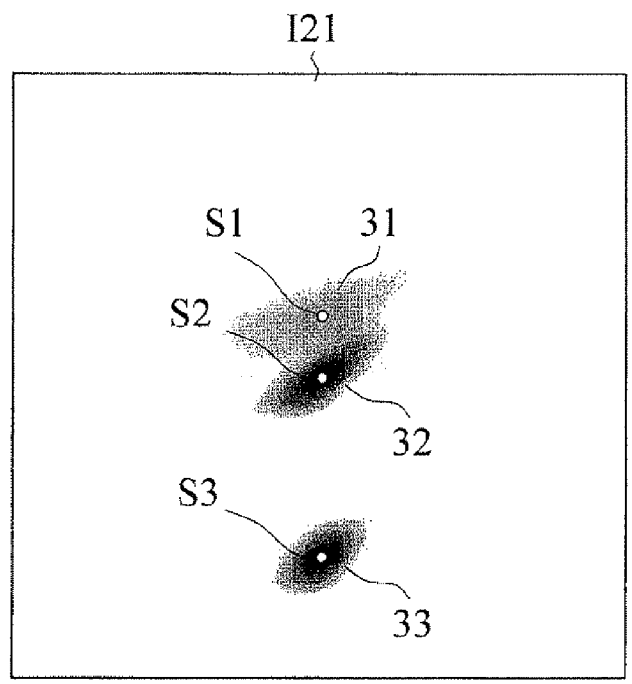
FIG. 8 is an image obtained by using long burst ultrasonic waves with the cycle number 6 of the imaging method of a structure defect and the imaging device of a structure defect shown in FIG. 5.

Thus, in the imaging device of a structure defect shown in FIG. 5, the long burst ultrasonic waves with the cycle number 6 are radiated by the ultrasonic transmitter 1 to the closed crack S1, the open crack S2, and the bottom surface S3. The subharmonic waves generated in the closed crack S1, the linear scattered waves generated in the open crack S2, and the linear scattered waves generated in the bottom surface S3 are received by the array receiver 2, and by performing the imaging by the imaging means on the basis of the reception signal, as shown in FIG. 8, an image I21 including the subharmonic waves and linear scattered waves is obtained. In the image I21, the closed crack S1 is imaged into 31, the open crack S2 into 32 and the bottom surface S3 into 33.

Figure 9:
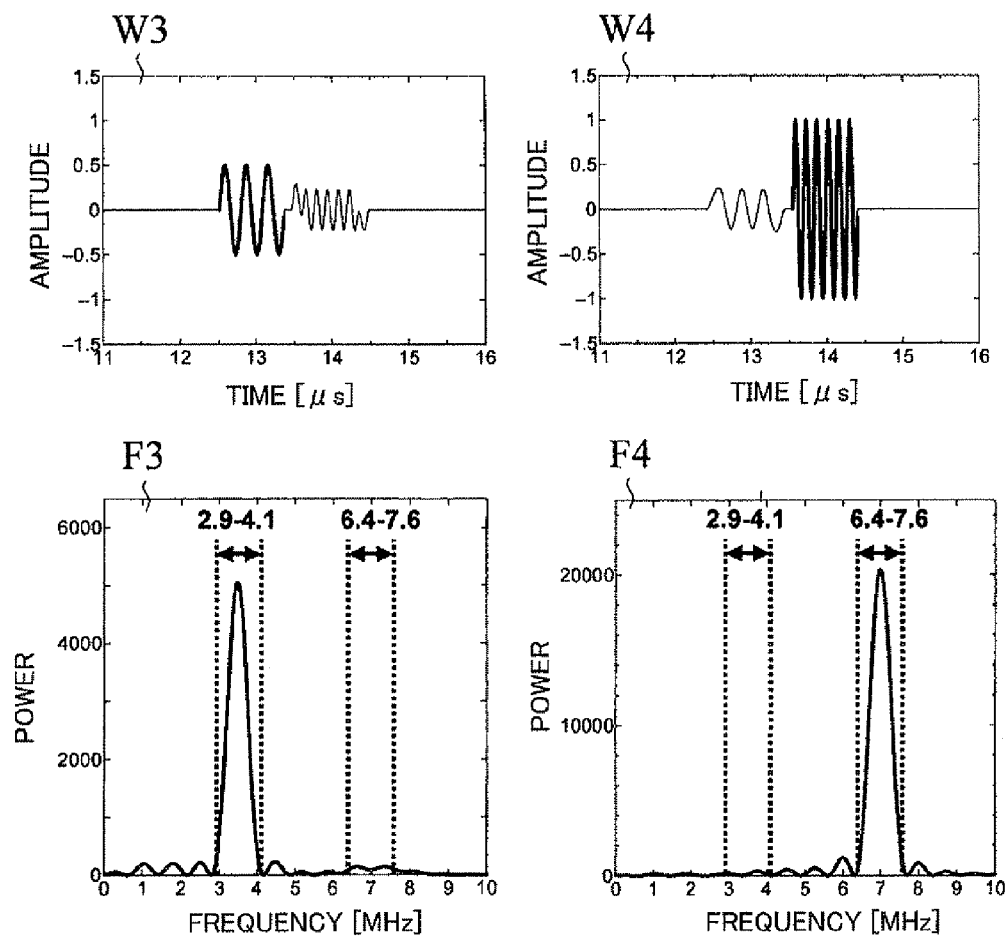
FIG. 9 are a phase-matched waveform W3 (bold line part) corresponding to a closed crack, power spectrum F3 thereof, a phase-matched waveform W4 (bold line part) corresponding to an open crack, and power spectrum F4 thereof if the long burst ultrasonic waves with the cycle number 6 is used in the imaging method of a structure defect and the imaging device of a structure defect shown in FIG. 8.

FIG. 9 illustrate a phase-matched waveform W3 (bold line part) in 41 imaged from the closed crack S1, power spectrum F3 thereof, a phase-matched waveform W4 (bold line part) in 42 imaged from the open crack 82, and power spectrum F4 thereof in the image I21. As shown by the power spectra F3 and F4 in FIG. 9, since the long burst ultrasonic waves are used, it is known that a frequency characteristic of a narrow band is provided as compared with the power spectra F1 and F2 shown in FIG. 6.

Figure 10:
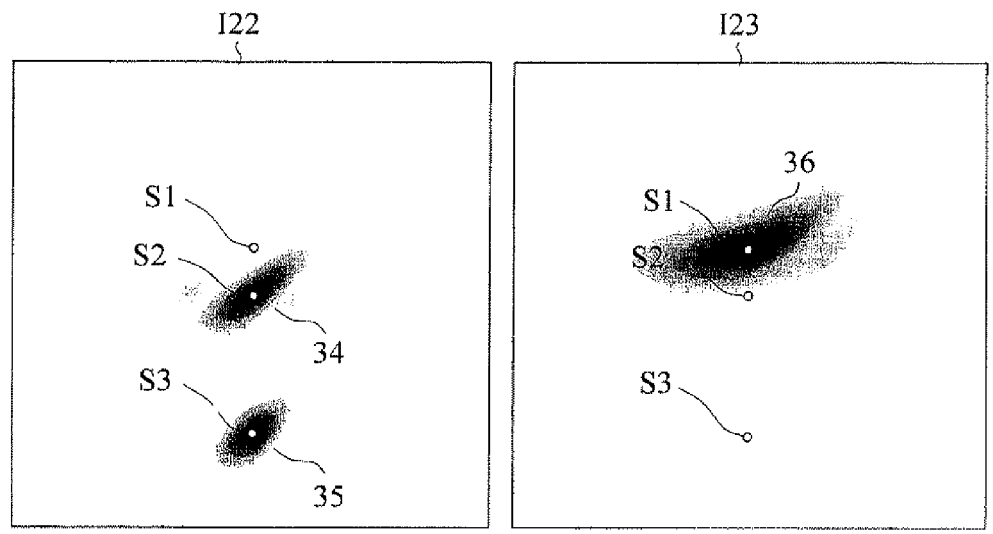
FIG. 10 are a fundamental wave image on the basis of a component of linear scattered waves extracted by a band-pass filter and a subharmonic wave image on the basis of subharmonic waves extracted by the band-pass filter if the long burst ultrasonic waves with the cycle number 6 are used in the imaging method of a structure defect and the imaging device of a structure defect shown in FIG. 8.

FIG. 10 illustrates a fundamental wave image I22 on the basis of a component of the linear scattered waves extracted by the band-pass filter and a subharmonic wave image I23 on the basis of the subharmonic waves extracted by the band-pass filter from the signal received by the array receiver 2. As shown in FIG. 10, in the fundamental wave image I22, 34 imaged from the open crack S2 and 35 imaged from the bottom surface S3 appeared. In the subharmonic wave image I23, due to use of the long burst ultrasonic waves, leakage of the linear scattered waves generated in the open crack S2 and the bottom surface S3 did not appear but only 36 imaged from the closed crack S1 appeared. Under this condition, as compared with the subharmonic wave image I13 with 2 cycles shown in FIG. 7, the intensity ratio between S1 and S2 in the subharmonic wave image I23 representing discrimination of the closed crack is improved to 7.1.

As a side effect, as 36 in the subharmonic wave image I23 shown in FIG. 10, spatial resolution is deteriorated as compared with the subharmonic wave image I13 shown in FIG. 7 due to extension of the image with increase of the cycle number. However, paying an attention to the fact that the extension is in a direction connecting the center of the array receiver 2 and the scattering source, a reversed arrangement of the imaging device of a structure defect shown in FIG. 5 is used here as shown in FIG. 11.

Figure 11:
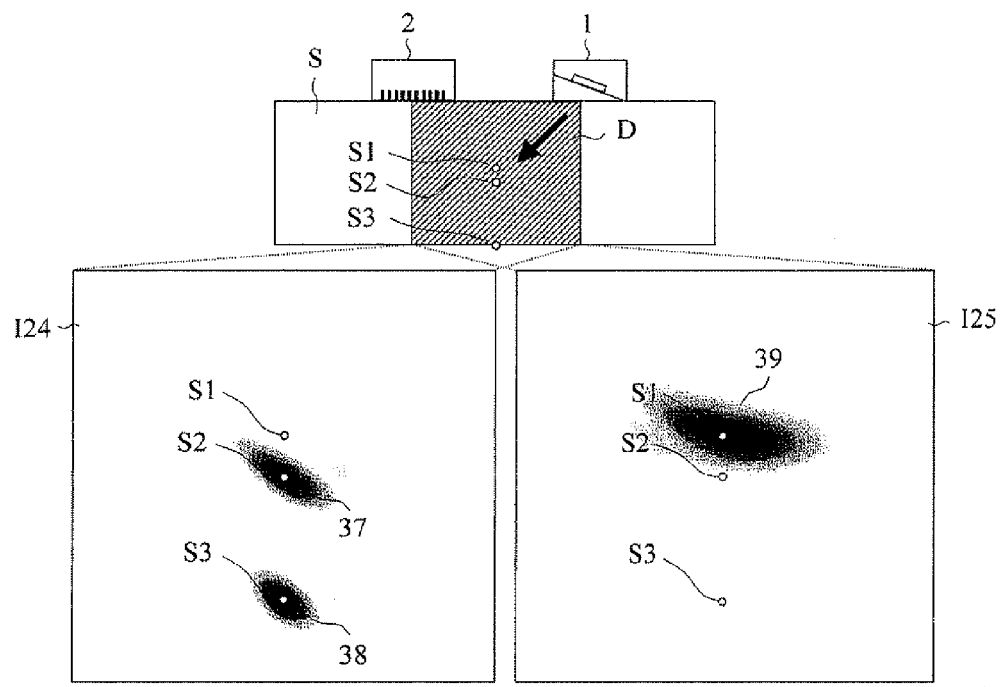
FIG. 11 is a longitudinal sectional view of reversed arrangement of FIG. 5 and a fundamental wave image and a subharmonic wave image obtained using the long burst ultrasonic waves with the cycle number 6, illustrating the imaging method of a structure defect and the imaging device of a structure defect of the embodiment of the present invention.

As shown in FIG. 11, the long burst ultrasonic waves with the cycle number 6 are radiated by the ultrasonic transmitter 1 to the closed crack S1, the open crack S2, and the bottom surface S3, and the subharmonic waves generated in the closed crack S1, the linear scattered waves generated in the open crack S2, and the linear scattered waves generated in the bottom surface S3 are received by the array receiver 2. From the signal received by the array receiver 2, a fundamental wave image I24 on the basis of the component of the linear scattered waves extracted by the band-pass filter and a subharmonic wave image I25 on the basis of the subharmonic waves extracted by the band-pass filter are imaged.

As shown in FIG. 11, in the fundamental wave image I24, 37 imaged from the open crack S2 and 38 imaged from the bottom surface S3 appeared. In the subharmonic wave image I25, due to use of the long burst ultrasonic waves, leakage of the linear scattered waves generated in the open crack S2 and the bottom surface S3 did not appear but only 39 imaged from the closed crack S1 appeared. Also, in the images I24 and I25, an image with an extending direction different from those of I22 and I23 shown in FIG. 10 was obtained.

Figure 12:
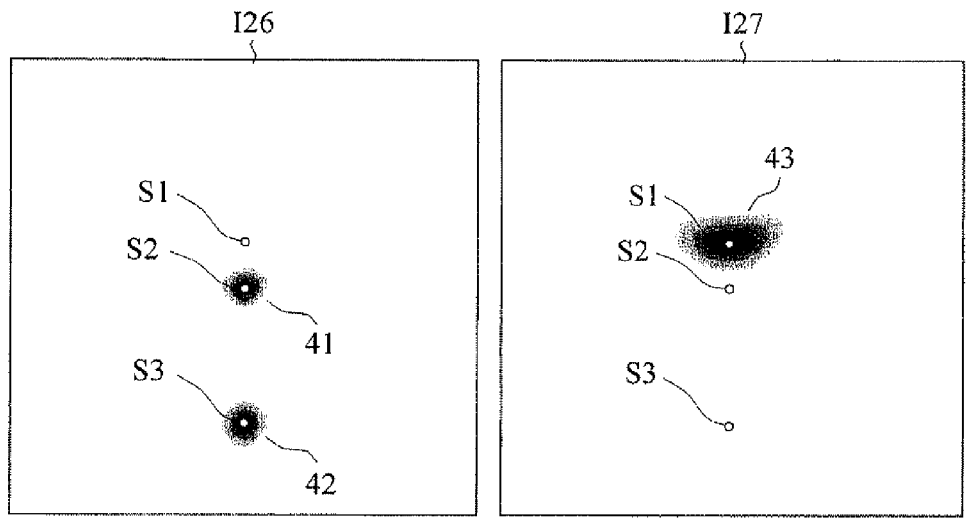
FIG. 12 is a fundamental wave image and a subharmonic wave image from which a common portion is extracted, respectively, from the fundamental wave image and the subharmonic wave image of the imaging method of a structure defect and the imaging device of a structure defect shown in FIGS. 10 and 11.

As shown in FIGS. 10 and 11, by executing integration processing by the extracting means of the signal processor 3 from the fundamental wave images I22 and I24 and subharmonic wave images I23 and I25 obtained from the arrangements of the ultrasonic transmitter 1 and the array receiver 2, different from each other, and by extracting the common portion, a fundamental wave image I26 and a subharmonic wave image I27 shown in FIG. 12 are obtained. As a result, in the fundamental wave image I26, common portions 41 and 42 are obtained, and the common portion 41 becomes an open part of the crack. In the subharmonic wave image I27, a common portion 43 becomes a closed part of the crack. As a result, extension of the image is reduced as compared with the subharmonic wave images I23 and I25, and it was shown that an image of only the crack closed part can be obtained. Under this condition, the intensity ratio between S1 and S2 in the subharmonic wave image I27 representing discrimination of a closed crack was 7.1.

Figure 13:
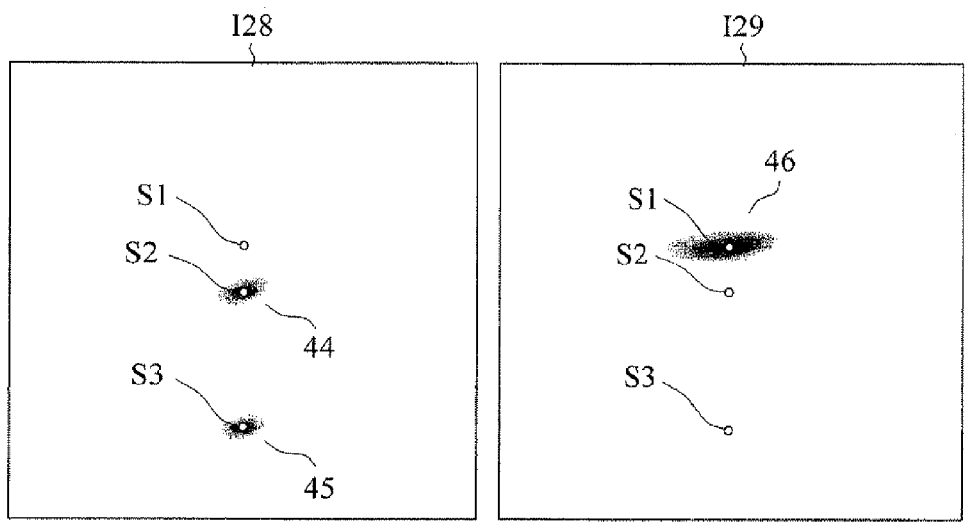
FIG. 13 is a fundamental wave image and a subharmonic wave image from which a common portion is extracted, respectively, from the fundamental wave image and the subharmonic wave image of the imaging method of a structure defect and the imaging device of a structure defect shown in FIGS. 7 and 10.
Figure 14:
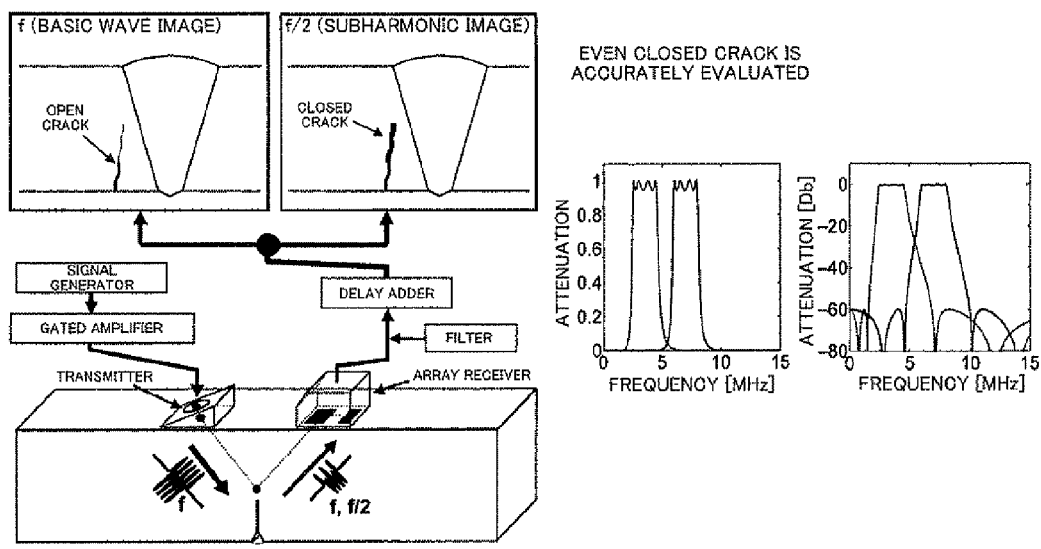
FIG. 14 is a prior-art principle diagram illustrating the SPACE using the phased array method for subharmonic waves.

As shown in FIGS. 7 and 10, by executing the integration processing by the extracting means of the signal processor 3 from the fundamental wave images I12 and I22 and the subharmonic wave images I13 and I23 obtained with different cycle numbers and by extracting a common portion, the fundamental wave image I28 and the subharmonic wave image I29 shown in FIG. 13 are obtained. As a result, common portions 44 and 45 are obtained in the fundamental wave image I28, and the common portion 44 becomes an open part of the crack. In the subharmonic wave image I29, a common portion 46 becomes a closed part of the crack. As a result, extension of the image is reduced as compared with the subharmonic wave image I23, and it was shown that an image of only the crack closed part can be obtained. Under this condition, the intensity ratio between S1 and S2 in the subharmonic wave image I29 representing discrimination of a closed crack was improved to 4.0 as compared with the subharmonic wave image I13 with 2 cycles.

As described above, even if two burst ultrasonic waves with different cycle numbers of the sine waves are radiated, according to the imaging method of a structure defect and the imaging device of a structure defect of the embodiment of the present invention, high frequency resolution and spatial resolution are provided, and discrimination between a closed crack and an open crack can be improved. Also, a defect such as a closed crack can be detected with high accuracy. As shown in FIG. 13, since the common portion of two images extending in the same direction, though the length is different, can be extracted, the image becomes larger than with the method in FIG. 12 in which the common portion of the images extending in the different directions is extracted, and the spatial resolution might be lowered.

In the imaging method of a structure defect and the imaging device of a structure defect of the embodiment of the present invention, the array receiver 2 can switch the reception sensor element to be used, and by switching the reception sensor elements to be used in the array receiver 2, the first arrangement and the second arrangement may be configured. In this case, two different images can be obtained without moving either of the ultrasonic transmitter 1 or the array receiver 2, and an image of a defect such as a closed crack with improved spatial resolution can be easily obtained.

Also, in the imaging method of a structure defect and the imaging device of a structure defect of the embodiment of the present invention, the band-pass filter may be configured so that only a frequency component of harmonic waves having a frequency integral multiple of the frequency of the sine waves contained in the burst ultrasonic waves corresponding to each reception signal subjected to the filter can be passed. In this case, too, using harmonic waves instead of the subharmonic waves, a defect such as a closed crack can be detected with particularly high accuracy, and frequency resolution can be improved.

In the imaging method of a structure defect and the imaging device of a structure defect of the embodiment of the present invention, the extracting means may be configured such that the common portion of each image is extracted by calculating a square root of the product of two digitized images. Also, the extracting means may be configured such that by giving intensity of the original image only to a common portion of a part to be one of two binarized images, the common portion of each image is extracted. In these cases, too, a common portion of each image can be easily extracted using a computer, and a defect such as a closed crack can be detected with high accuracy.

It is obvious that the imaging method of a bubble or a lesion and the imaging device of a bubble or a lesion of the embodiment of the present invention can be similarly applied to improvement of selectivity of an imaging agent air bubble or a lesion of a living tissue using harmonic/subharmonic waves, not only to a structure defect, by reading the "structure" as "tissue" and the "defect" as "a bubble or a lesion" in the description of the imaging method of a structure defect and the imaging device of a structure defect of the embodiment of the present invention.

REFERENCE SIGNS LIST 1 ultrasonic transmitter
2 array receiver
3 signal processor
A first arrangement
B second arrangement
C1 open crack
C2 closed crack
S sample
S1 closed crack
S2 open crack
S3 bottom surface

The invention claimed is:

1. An imaging method of a structure defect that detects a defect such as a crack contained in a structure, having an ultrasonic transmitter that radiates burst ultrasonic waves composed of sine waves with a predetermined cycle number and an array receiver having a plurality of reception sensor elements, comprising:

in first arrangement in which said ultrasonic transmitter and said array receiver are arranged at predetermined positions with respect to said defect, a first reception process of receiving scattered waves from said defect of said burst ultrasonic waves radiated from said ultrasonic transmitter to said structure by said array receiver so as to obtain a first reception signal;

a first imaging process in which said first reception signal is subjected to a band-pass filter that passes a specific frequency component and is shifted by different time according to the position of each of the reception sensor elements of said array receiver and then, added so as to obtain a first processing signal, and a first image of said defect is obtained on the basis of said obtained first processing signal;

in second arrangement in which at least one of the positions of said ultrasonic transmitter and said array receiver with respect to said defect is different, a second reception process of receiving the scattered waves from said defect of said burst ultrasonic waves radiated from said ultrasonic transmitter to said structure by said array receiver so as to obtain a second reception signal;

a second imaging process in which said second reception signal is subjected to said band-pass filter and is shifted by different time according to the position of each of the reception sensor elements of said array receiver and then, added so as to obtain a second processing signal, and a second image of said defect is obtained on the basis of said obtained second processing signal; and an extraction process of extracting a common portion of said first image and said second image.

2. An imaging method of a structure defect that detects a defect such as a crack contained in a structure, having an ultrasonic transmitter that radiates burst ultrasonic waves composed of sine waves with an arbitrary cycle number and an array receiver having a plurality of reception sensor elements, comprising:

a first reception process in which first burst ultrasonic waves composed of sine waves with a predetermined cycle number are radiated from said ultrasonic transmitter to said structure, and scattered waves from said defect of said first burst ultrasonic waves are received by said array receiver so as to obtain a first reception signal;

a first imaging process in which said first reception signal is subjected to a band-pass filter that passes a center frequency component of said sine waves, a frequency component of the integral multiple thereof or a frequency component of an integral fraction thereof and shifted by different time according to the position of each of the reception sensor elements of said array receiver and then, added so as to obtain a first processing signal and on the basis of said obtained first processing signal, a first image of said defect is obtained;

a second reception process in which second burst ultrasonic waves composed of sine waves of a cycle number different from said predetermined cycle number are radiated from said ultrasonic transmitter to said structure, and the scattered waves from said defect of said second burst ultrasonic waves are received by said array receiver so as to obtain a second reception signal;

a second imaging process in which said second reception signal is subjected to said band-pass filter and shifted by different time according to the position of each of the reception sensor elements of said array receiver and then, added so as to obtain a second processing signal, and on the basis of said obtained second processing signal, a second image of said defect is obtained; and an extraction process of extracting a common portion of said first image and said second image.

3. The imaging method of a structure defect according to claim 1, wherein the cycle number of sine waves contained in said burst ultrasonic waves is 4 or more.

4. The imaging method of a structure defect according to claim 2, wherein the cycle number of sine waves contained in said first burst ultrasonic waves is 4 or more and the cycle number of the sine waves contained in said second burst ultrasonic waves is 3 or less.

5. The imaging method of a structure defect according to claim 1, wherein said first arrangement and said second arrangement are configured by switching the reception sensor elements used in said array receiver.

6. The imaging method of a structure defect according to claim 1, wherein a band width of said band-pass filter is set in inverse proportion to the cycle number of sine waves contained in the burst ultrasonic waves corresponding to said first reception signal or said second reception signal subjected to the filter.

7. The imaging method of a structure defect according to claim 1, wherein the number of said reception sensor elements of said array receiver is determined so that said first image and said second image are in the shape extending depending on the cycle number of the sine waves contained in the burst ultrasonic waves corresponding to each image in the direction connecting the center of said array receiver and said defect.

8. The imaging method of a structure defect according to claim 1, wherein said band-pass filter passes only a frequency component of harmonic waves having a frequency of integral multiple of the frequency of the sine waves contained in the burst ultrasonic waves corresponding to said first reception signal or said second reception signal subjected to the filter or of subharmonic waves having a frequency of an integral fraction of the frequency of the sine waves contained in the burst ultrasonic waves corresponding to said first reception signal or said second reception signal subjected to the filter.

9. The imaging method of a structure defect according to claim 1, wherein said extraction process is configured such that by calculating a product of said digitized first image and said second image or by calculating a square root of the product, or by giving intensity of said original first image or said second image only to a common part of a portion to become one of said binarized first image or said binarized second image, the common portion of said first image and said second image is extracted.

10. An imaging device of a structure defect that detects a defect such as a crack contained in a structure, comprising:

an ultrasonic transmitter that radiates burst ultrasonic waves composed of sine waves with an arbitrary cycle number;

an array receiver having a plurality of reception sensor elements disposed capable of receiving scattered waves from said defect of said burst ultrasonic waves radiated from said ultrasonic transmitter to said structure;

imaging means in which a reception signal received by each of the reception sensor elements of said array receiver is subjected to a band-pass filter that passes a specific frequency component and shifted by different time according to the position of each of the reception sensor elements of said array receiver and then, added so as to obtain a processing signal and on the basis of said obtained processing signal, an image of said defect is obtained; and extracting means that extracts a common portion of two images different from each other obtained by said imaging means.

11. The imaging device of a structure defect according to claim 10, wherein said ultrasonic transmitter is configured to radiate burst ultrasonic waves with sine waves of a cycle number of 4 or more; and said imaging means is configured to obtain two images different from each other for two cases in which at least one of positions of said ultrasonic transmitter and said array receiver is different with respect to said defect.

12. The imaging device of a structure defect according to claim 10, wherein said imaging means is configured to obtain two images different from each other for cases in which the cycle number of sine waves contained in the burst ultrasonic waves radiated by said ultrasonic transmitter is 4 or more and 3 or less.

13. The imaging device of a structure defect according to claim 10 wherein said array receiver can switch the reception sensor elements to be used.

14. The imaging device of a structure defect according to claim 10, wherein in said imaging means, a band width of said band-pass filter is in inverse proportion to the cycle number of sine waves contained in the burst ultrasonic waves corresponding to said reception signal subjected to the filter.

15. The imaging device of a structure defect according to claim 10, wherein in said array receiver, the number of said reception sensor elements is determined so that said two images are in the shape extending depending on the cycle number of the sine waves contained in the burst ultrasonic waves corresponding to each image in the direction connecting the center of said array receiver and said defect.

16. The imaging device of a structure defect according to claim 10, wherein said band-pass filter is configured to pass only a frequency component of harmonic waves having a frequency of integral multiple of the frequency of the sine waves contained in the burst ultrasonic waves corresponding to said reception signal subjected to the filter or of subharmonic waves having an integral fraction of the frequency of the sine waves contained in the burst ultrasonic waves corresponding to said reception signal subjected to the filter.

17. The imaging device of a structure defect according to claim 10, wherein
said extracting means is configured such that by calculating a product of said digitized two images or by calculating a square root of the product, or by giving intensity of the original image only to a common part of a portion to become one of said binarized two images, the common portion of each image is extracted.

18. An imaging method of a bubble or a lesion that detects a bubble or a lesion contained in a tissue, having an ultrasonic transmitter that radiates burst ultrasonic waves composed of sine waves with an arbitrary cycle number and an array receiver having a plurality of reception sensor elements, comprising:
a first reception process in which first burst ultrasonic waves composed of sine waves with a predetermined cycle number are radiated from said ultrasonic transmitter to said tissue, and scattered waves from said bubble or lesion of said first burst ultrasonic waves are received by said array receiver so as to obtain a first reception signal;
a first imaging process in which said first reception signal is subjected to a band-pass filter that passes a center frequency component of said sine waves, a frequency component of the integral multiple thereof or a frequency component of an integral fraction thereof and shifted by different time according to the position of each of the reception sensor elements of said array receiver and then, added so as to obtain a first processing signal and on the basis of said obtained first processing signal, a first image of said bubble or lesion is obtained;
a second reception process in which second burst ultrasonic waves composed of sine waves of a cycle number different from said predetermined cycle number are radiated from said ultrasonic transmitter to said tissue, and the scattered waves from said bubble or lesion of said second burst ultrasonic waves are received by said array receiver so as to obtain a second reception signal;
a second imaging process in which said second reception signal is subjected to said band-pass filter and shifted by different time according to the position of each of the reception sensor elements of said array receiver and then, added so as to obtain a second processing signal, and on the basis of said obtained second processing signal, a second image of said bubble dr lesion is obtained; and
an extraction process of extracting a common portion of said first image and said second image.

19. An imaging device of a bubble or a lesion that detects a bubble or a lesion contained in a tissue, comprising:
an ultrasonic transmitter that radiates burst ultrasonic waves composed of sine waves with an arbitrary cycle number;
an array receiver having a plurality of reception sensor elements disposed capable of receiving scattered waves from said bubble or lesion of said burst ultrasonic waves radiated from said ultrasonic transmitter to said tissue;
imaging means in which a reception signal received by each of the reception sensor elements of said array receiver is subjected to a band-pass filter that passes a specific frequency component and shifted by different time according to the position of each of the reception sensor elements of said array receiver and then, added so as to obtain a processing signal and on the basis of said obtained processing signal, an image of said bubble or lesion is obtained; and
extracting means that extracts a common portion of two images different from each other obtained by said imaging means.

* * * * *